United States Patent [19]

Wilhelm et al.

[11] Patent Number: 5,399,769
[45] Date of Patent: Mar. 21, 1995

[54] PREPARATION OF METHYLAMINES USING SHAPE SELECTIVE CHABAZITES

[75] Inventors: Frederick C. Wilhelm, Zionsville; Gene E. Parris, Revere; Brent A. Aufdembrink, Jim Thorpe; Thomas R. Gaffney, Allentown, all of Pa.

[73] Assignee: Air Products and Chemicals, Inc., Allentown, Pa.

[21] Appl. No.: 253,872

[22] Filed: Jun. 3, 1994

Related U.S. Application Data

[63] Continuation-in-part of Ser. No. 86,497, Jul. 1, 1993, abandoned.

[51] Int. Cl.⁶ .............................................. C07C 209/16
[52] U.S. Cl. ...................................... 564/480; 564/479
[58] Field of Search .................................. 564/479, 480

[56] References Cited

U.S. PATENT DOCUMENTS

| | | | |
|---|---|---|---|
| 3,384,667 | 5/1968 | Hamilton | 260/585 |
| 4,082,805 | 4/1978 | Kaeding | 208/111 |
| 4,205,012 | 5/1980 | Parker | 252/455 |
| 4,254,061 | 3/1981 | Weigert | 564/479 |
| 4,313,003 | 1/1982 | Weigert | 564/463 |
| 4,398,041 | 8/1983 | Cochran et al. | 564/479 |
| 4,434,300 | 2/1984 | Deeba et al. | 564/479 |
| 4,458,092 | 7/1984 | Deeba et al. | 564/479 |
| 4,485,261 | 11/1984 | Ashina et al. | 564/479 |
| 4,602,112 | 7/1986 | Gier et al. | 564/474 |
| 4,737,592 | 4/1988 | Abrams et al. | 564/479 |

*Primary Examiner*—Glennon H. Hollrah
*Assistant Examiner*—Scott C. Rand
*Attorney, Agent, or Firm*—Russell L. Brewer; William F. Marsh

[57] ABSTRACT

This invention relates to a process for producing a non-equilibrium distribution of methylamines by the catalyzed reaction of methanol and/or dimethyl ether with ammonia and by the catalytic reforming of a methylamine containing feedstock. One process selectively affords a reaction product enriched in mono and dimethylamines and low in trimethylamine, at high conversion of methanol or dimethylether. A variation of the process effects reforming a methylamine containing feedstock, optionally containing ammonia over a catalyst. The key to achieving this low TMA selectivity at high conversion resides in the use of a microporous zeolite, preferably chabazite, catalyst having a geometric selectivity index (GSI) less about 3, a shape selectivity index (SSI) greater than about 5 and a sorption capacity for 1-PrOH of at least 0.5 mmol/g.

21 Claims, 3 Drawing Sheets

PREPARATION OF METHYLAMINES USING SHAPE SELECTIVE CHABAZITES

CROSS REFERENCE TO RELATED APPLICATIONS

This application is a continuation-in-part application of commonly assigned U.S. application Ser. No. 08/086,497, having a filing date of Jul. 1, 1993, now abandoned. The subject matter is incorporated by reference.

FIELD OF THE INVENTION

This invention relates to processes for the preparation of methylamines from methanol or dimethylether and ammonia using microporous compositions as catalyst.

BACKGROUND OF THE INVENTION

The reaction of methanol and ammonia to produce methylamines, comprising a mixture of mono-, di- and trimethylamine, is a well known reaction. The reaction product is an equilibrium mixture with about 35 wt % of the reaction product consisting of monomethylamine (MMA), 27 wt % dimethylamine (DMA), and 38 wt % trimethylamine (TMA) produced at a temperature of 350° C., 1 atmosphere pressure and an ammonia to methanol ratio (N/R) of 3.5. Substantial process efforts have been made for the development of processes which would alter the product slate resulting from the reaction of methanol and ammonia. Process variables influencing product slate, although limited, include space time, ammonia to methanol molar ratio and temperature. Product slate modifications primarily have been made via shape selective catalysts such as zeolites.

Representative patents which illustrate various processes for the production of a methylamine reaction product having non equilibrium levels of MMA, DMA and TMA by the reaction of methanol and ammonia are as follows:

U.S. Pat. No. 4,485,261 discloses a process for the preparation of a methylamine reaction product rich in DMA and lean in TMA which comprises introducing a mixture of methylamines and ammonia to a porous; solid acid catalyst comprising silica, alumina, Y and X type zeolites, thereby forming a first reaction product and then subjecting at least a part of the reaction product to a catalytic reforming reaction in the presence of ammonia and a crystalline alumino-silicate having a pore size of 3 to 8 Å. A variety of catalysts having a pore size of 3 to 8 Å is set forth, and these catalysts include clinoptilolite, erionite, mordenite, chabazite and various synthetic zeolites. U.S. Pat. No. 4,205,012 discloses a process for producing amines by the reaction of an alkanol with ammonia, e.g., the manufacture of methylamines by the reaction of methanol and ammonia in the presence of an FU-1 zeolite, said FU-1 zeolite having essentially all of the sodium cations replaced by bivalent or trivalent cations.

U.S. Pat. No. 4,602,112 discloses a process for producing DMA in high selectivity by the reaction of methanol or dimethylether and ammonia in the presence of an acidic H-ZSM-5 zeolite catalyst.

U.S. Pat. No. 3,384,667 discloses the alkylation of ammonia in the presence of a dehydrated naturally occurring crystalline alumino-silicate catalyst having pores of a diameter permitting absorption of primary and secondary, but not tertiary, amine products. Examples of natural zeolites include ferrierites, chabazite, erionite and mordenite.

U.S. Pat. No. 4,737,592 discloses a process for producing a reaction product rich in DMA by reacting methanol and/or dimethylether and ammonia in the presence of an acidic zeolite catalyst selected from the group consisting of natural, H-exchanged and M-exchanged chabazites, each having a geometric selectivity index (GSI) greater than about 3. Alkali metal ions suited for exchange include sodium, potassium, rubidium and cesium.

U.S. Pat. Nos. 4,458,092; 4,398,041 and 4,434,300 disclose processes for producing methylamine by carrying out the reaction utilizing zeolite type catalysts. The '092 patent discloses the use of a highly acidic dehydrated alumino-silicate catalyst exchanged with a rare earth or hydrogen metal ion exchanged Y-zeolite. The '300 patent discloses the preparation of the amines using macroporous H-chabazite-erionite as the preferred amination catalyst. Anaconda chabazite-erionite was used as a specific catalyst and that catalyst system achieved high methanol conversion rates with minimal TMA production.

U.S. Pat. Nos. 4,254,061 and 4,313,003 disclose the production of a methylamine rich in MMA ('061) and DMA ('003). The '061 patent discloses the reaction of methanol and ammonia in the presence of mordenite, erionite, clinoptilolite, etc. to produce MMA, while the '003 discloses the reaction of MMA and ammonia in the presence of the '061 patent catalysts to produce a reaction product rich in DMA.

U.S. Pat. No. 4,082,805 discloses the production of amines by the reaction of $C_1$ to $C_5$ alcohols or ethers with ammonia in the presence of a crystalline alumino-silicate having the structure ZSM-5, ZSM-11 or ZSM-21.

SUMMARY OF THE INVENTION

This invention relates to an improved process for the production of a methylamine reaction product having nonequilibrium levels of TMA. One of the basic processes for producing a methylamine reaction product with excellent conversion of methanol/dimethylether and reduced trimethylamine content comprises reacting methanol/dimethylether with ammonia, monoethylamine, dimethylamine and trimethylamine in the presence of a zeolitic catalyst. Alternatively, another process for producing a methylamine-rich reaction product relies on reforming a monomethylamine containing feedstock over a catalyst. One part of the improvement in the basic process resides in producing a reaction product with reduced levels of trimethylamine and excellent conversion of methanol/dimethylether resides in the utilization of a zeolite catalyst consisting essentially of a zeolite, preferably a chabazite, having a shape selectivity index (SSI) of above about 5, a GSI of less than 3 and a 1-propanol sorption value of greater than 0.5 mmol/g. The shape selective zeolites or synthetic chabazites typically are exchanged with alkali metal ions such as sodium, potassium, rubidium and cesium. A second part of the improvement in the basic process resides in passing a feedstock comprising monomethylamine over such catalyst thereby reforming such monomethylamine to a product slate rich in dimethylamine.

There are several significant advantages which can be achieved through the utilization of the zeolites and synthetic chabazites having an SSI index and propanol sorption value as stated and these advantages include:

an ability to produce a reaction product rich in mono and dimethylamine with reduced levels of trimethylamine;

an ability to produce methylamines via the amination of methanol with excellent rates of reaction;

an ability to produce a reaction product comprising methylamines with excellent methanol conversions;

an ability to produce a reaction product having nonequilibrium levels of mono, di and TMA distribution;

an ability to operate a methanol amination process over a substantial length of time without catalyst deactivation;

an ability to operate over an extended period of time; and ability to recycle a monomethylamine containing feedstock over the catalyst to obtain a nonequilibrum product slate.

DETAILED DESCRIPTION OF THE INVENTION

One of the basic routes for producing alkylamines is through the amination of alkanols and alkylethers. The route for producing methylamines generally involves the reaction of methanol (MeOH) and/or dimethylether (DME) with ammonia, monomethylamine (MMA), dimethylamine (DMA) or trimethylamine (TMA), depending on available feeds and desired product slate, under conditions sufficient to effect amination. Typically, the nitrogen/carbon (N/R) molar ratio will range from about 0.2 to about 10, preferably 1 to 5, with reaction temperatures ranging from about 225° C. to 450° C. (preferably 250° C. to 375° C.). Reaction pressures may vary, but typically range from 50 to 1000 psig, preferably 150 to 500 psig, at total feed space velocities of from about 200 to 8000 $hr^{-1}$, preferably 500 to 5000 $hr^{-1}$. The term "space velocity" or GHSV, is defined as the ratio of the feed rate in $cm^3$ gas at STP/hr to the catalyst bed volume in $cm^3$.

The resulting conversion of methanol and/or DME to methylamines generally will range from about 50% to 100% (on a molar basis of methanol) with total selectivity to methyl amines greater than 95 wt % and low TMA being 20 wt % or less, and generally less than 15 wt %. Typically, the weight percentage of MMA in the reaction product will range from 36 to 50 wt %, and the percentage of DMA in the reaction product will range from 25 to 60 wt %.

Another feedstock suited for the practice of the process is one containing monomethylamine. The monomethylamine is reformed over the catalyst to a product slate rich in dimethylamine. Optionally, ammonia and other components, e.g., trimethylamine can be present in the feedstock. But no significant advantages are seen in the product slate when trimethylamine is incorporated into the feedstock.

The key to the amination process for producing high conversion and excellent reaction rates with low TMA production resides in the use of a catalyst system comprising a microporous catalyst having a geometric selectivity index (GSI) less than 3, a shape selectivity index (SSI) greater than about 5 and which sorbs at least about 0.5 mmol 1-PrOH per gram catalyst (3 wt % 1-PrOH). The preferred catalyst system is one consisting of a synthetic chabazite having an SSI of about 7 to 25. The term "shape selectivity index" (SSI) is defined by the formula:

SSI=Quantity of 1-PrOH sorbed divided by the quantity of 2-PrOH sorbed by the catalyst at 20° C. over a 24 hour period and the relative pressure P/Po is 0.5. The sorption is expressed in wt %, i.e., grams sorbate per 100 grams of zeolite catalyst.

Many of the prior art processes that carried out methanol amination in the presence of chabazite catalyst systems are generated from naturally occurring chabazites. The key to the success of natural chabazites resided in a geometric selectivity index (GSI) as noted in U.S. Pat. No. 4,737,592, where the GSI must be greater than about 3. The geometric selectivity index was determined by the formula:

GSI=net sorption of methanol (MeOH) divided by the net sorption of 1-PrOH (n-PrOH) measured at 25° C. and relative pressure P/Po of 0.1 to 0.5 for a period of 20 hours exposure to the sorbate vapor. The sorption is expressed in wt %, i.e., grams sorbate per 100 grams of zeolite.

It has been found that GSI is not altogether predictable for determining the effectiveness of the catalyst in terms of selectivity or activity. Synthetic chabazite catalysts, in particular, do not follow this parameter in terms of selectivity and activity. It has been found that the activity and shape selectivity of zeolites and particularly chabazites, as a catalyst can be predicted with greater accuracy through the use of a parameter referred to as shape selectivity index (SSI) and another relating to 1-propanol sorption. SSI can assess the size and shape of either pore mouth opening or cavity while GSI evaluates cavity size using molecular packing. As the SSI value increases, the size and/or shape of the microporous structure preferentially excludes 2-PrOH to a greater extent than 1-PrOH. SSI, since it uses a branched alcohol 2-PrOH, as opposed to a straight chain alcohol, places a greater emphasis on the size and shape of the catalyst pore mouth than on the cavity, although it accounts for both effects. GSI uses straight chain alcohols in its determination and, therefore, it is more useful for assessing how molecules pack within a microporous cavity and does not indicate an ability of the catalyst to permeate reactant or product from within the cage structure. A correlation between the two concepts is apparent if the catalysts differ only in cavity size via cation occupancy or the lattice constant changes.

The requirement of a minimum sorption value of 1-propanol for the catalyst provides a measure of the ability of the catalyst to achieve high methanol reaction rates, e.g., rates leading to greater than 50% and generally greater than 75% conversion at operating temperature and space velocity. A catalyst having low propanol sorption values, although having a high SSI or GSI may provide shape selectivity but generally will also exhibit poor methanol/dimethylether conversion.

Metal cations in the zeolitic structure have an influence on both the SSI and activity of the catalyst. Large metal cations limit the sorption capacity of the zeolite framework and reduce its ability to sorb 2-propanol. Cations, e.g., H may not be positioned or occupy sufficient space within the zeolitic framework thus leading to zeolites having low SSI values and to equilibrium distributions of methyl amines. Cations should be selected such that the zeolite or chabazite has an SSI within the preferred range and sufficient acidity to maintain activity. Representative cations which may be used include H, Li, Na, K, Rb, Cs, Mg, Ca, Ba, Al, Ga, Fe, Sr, La, Cu, Zn, Ni, B, Ce, Sn and Ru. Of these, the alkali metals, K and Na, are preferred.

Methods of preparation of such chabazite materials are known and examples are found in U.S. Pat. No. 4,925,460 which is incorporated by reference. After preparation, the chabazite preferably is heated to a temperature of at least 375° C. to effect the calcination of the catalyst system. Although both the uncalcined and calcined catalyst systems can be utilized in the practice of the methanol amination process, the calcined chabazite affords higher methanol conversion rates than does the uncalcined chabazite catalyst system, and the calcined synthetic chabazite system also affords reduced levels of TMA.

As with all shape selective catalysts, there is an ability to "override" the shape selectivity afforded by the catalyst. When that happens, the product slate approaches an equilibrium distribution. Shape selectivity is diminished when the catalytic effect is shifted from the cavity network of the zeolite to surface catalysis. There are many factors which can lead to an equilibrium distribution of methylamine product via a shape selective catalyst and these include excessive temperature, low space velocity, catalyst coking and the like. Reaction temperature, in particular, is the primary method of shifting the product slate from that of a shape selective distribution toward an equilibrium distribution. The following examples are provided to illustrate various embodiments of the invention and comparisons to the prior art. All percentages are expressed as weight percentages unless otherwise specified.

EXAMPLE 1

Preparation of a Synthetic Potassium Chabazite

A sample of potassium chabazite was prepared by the general procedure of Coe and Gaffney in U.S. Pat. No. 4,925,460. More specifically, 48 gms of ammonium- Y zeolites, LZY62 extrudates from UOP were calcined at 500° C. for 2 hrs, then cooled and humidified. The humidified extrudates were then added to and digested in a premixed solution of 189 gms of colloidal silica (14% $SiO_2$) and 672 ml of 1M KOH. Nine (9) such digestions were done simultaneously in separate Nalgene bottles. The mixture was held at 95°–100° C. for 96 hrs. The solids were recovered and washed with deionized water until a pH of 7 was reached. Elemental analysis gave the following composition as weight % of the oxides: 17.80% $K_2O$, 0.02% $Na_2O$, 24.30% $Al_2O_3$ and 56.50% $SiO_2$. The bulk Si/Al ratio was 1.97 and the framework Si/Al ratio by $^{29}Si$ MASNMR was 2.4. X-ray diffraction spectroscopy showed that the product was spectroscopically pure chabazite with no trace of Y type zeolite contaminant. The ratio of (K+Na) to total Al content indicates that about 80% of the Al was in the zeolite framework.

EXAMPLE 2

Preparation of an Ammonium Exchanged Synthetic Chabazite

A sample of ammonium exchanged chabazite was prepared by ion exchange of a portion of the K-Chabazite sample prepared in Example 1. The hydrated K-Chabazite was added to a 30 wt % $NH_4NO_3$ solution at a ratio of 2 ml solution to 1 gm chabazite, then heated to 95°–100° C. and held for 2 hrs, then the solid was recovered and thoroughly washed with deionized water. This exchange and wash procedure was repeated 5 additional times. After drying at 110° C., 450 gms of $NH_4$ chabazite product was recovered. The residual K comprised approximately 11% of the ion exchange capacity.

EXAMPLE 3

Preparation of a 95% Potassium Exchanged Synthetic Chabazite

A sample of potassium exchanged chabazite was prepared by ion exchange of a portion of the $NH_4$-Chabazite sample prepared in Example 2. 30 gms of the dried $NH_4$-Chabazite was humidified, added to 300 ml of 1M $KNO_3$ solution at 95°–100° C. for 2 hrs, then the solid was recovered and washed with deionized water. This exchange and wash procedure was repeated one additional time. Elemental analysis of the product gave the following composition as weight % of the oxides: (17.17% $K_2O$, <0.02% $Na_2O$, 24.6% $Al_2O_3$ and 56.60% $SiO_2$. The K content of the sample comprised approximately 94.5%, of the ion exchange capacity.

EXAMPLE 4

Preparation of a 58% Sodium Exchanged Synthetic Chabazite

A sample of sodium exchanged chabazite was prepared by ion exchange of a portion of the $NH_4$-chabazite sample prepared in Example 2. 50 gms of the dried $NH_4$ Chabazite was humidified, added to 300 ml of 1M $NaNO_3$ solution at 95°–100° C. for 2 hrs, then the solid was recovered and washed with deionized water. This exchange and wash procedure was repeated 1 additional time. Elemental analysis of the product gave the following composition as weight % of the oxides: 1.32% $K_2O$, 7.63% $Na_2O$, 27.20% $Al_2O_3$ and 64.20% $SiO_2$. The Na and K contents of the sample comprised approximately 57.5% and 6.5%, respectively, of the ion exchange capacity.

EXAMPLE 5

Preparation of a 99+% Sodium Exchanged Synthetic Chabazite

A sample of sodium exchanged chabazite was prepared by ion exchange of a portion of the $NH_4$-chabazite sample prepared in Example 2. 30 gms of the dried $NH_4$-chabazite was humidified, added to 1000 ml of 1M $NaNO_3$ solution at 95°–100° C. for 2 hrs, then the solid was recovered and washed with distilled, deionized water. This exchange and wash procedure was repeated 5 additional times. Elemental analysis of the product gave the following composition as weight percent of the oxides: 0.05% $K_2O$, 12.66% $Na_2O$, 25.80% $Al_2O_3$ and 61.20% $SiO_2$. The Na and K contents of the sample comprised approximately 99+% and 0.5%, respectively, of the ion exchange capacity.

EXAMPLE 6

Preparation of a 66% Sodium Exchanged Synthetic Chabazite

The preparation of the sodium exchanged chabazite involved a three step procedure. These steps are:

A. A sample of potassium chabazite was prepared by the general procedure of Example 1. 160 gms of LZY64 extrudates obtained was calcined at 500° C. for 2 hrs, then cooled and humidified. The humidified extrudates were then added to and digested in a premixed solution of 630 gms of Nalco TM 2326 colloidal silica (14% $SiO_2$) and 2240 ml of 1M KOH. Three such digestions were done simultaneously in separate Nalgene bottles. The mixtures were held at 95°–100° C. for 96 hrs. The solids were recovered, combined and washed with deionized water until a pH of 7 was reached then dried at 110° C. The ratio of K+Na to total Al content indicated that 84% of the Al was in the zeolite framework.

B. A sample of ammonium exchanged chabazite was prepared by ion exchange of a portion of the K-chabazite sample synthesized in step A. 50 gms of the dried $NH_4$-chabazite was humidified, added to 125 ml of 30 wt % $NH_4NO_3$ solution at 95°–100° C. for 2 hrs, then the solid was recovered and thoroughly washed with deionized water. This exchange and wash procedure was repeated five additional times.

C. A sodium exchanged chabazite was prepared by ion exchange of the $NH_4$-chabazite sample prepared in accordance with step B. All of the hydrated $NH_4$-chabazite was added to 300 ml of a 1M $NaNO_3$ solution at 95°–100° C. for 2 hrs, then the solid was recovered and washed with deionized water. This exchange and wash procedure was repeated 1 additional time. Elemental analysis of the product gave the following composition as weight % of the oxides: 0.28% $K_2O$, 8.46% $Na_2O$, 25.20% $Al_2O_3$ and 66.10% $SiO_2$. The Na and K contents of the sample comprised approximately 66% and 1.4%, respectively, of the ion exchange capacity.

EXAMPLE 7

Preparation of an Potassium Exchanged Synthetic Chabazite

A sample of potassium chabazite was prepared by the digestion procedure of Example 6 except that a different lot of LZY64 was used.

EXAMPLE 8

Preparation of a 80% Sodium Exchanged Synthetic Chabazite

A sample of sodium exchanged chabazite was prepared by ion exchange of a portion of the K-chabazite sample prepared above in Example 7. 50 gms of the dried K-chabazite was humidified, added to 1665 ml of 1M $NaNO_3$ solution at 95°–100° C. for 2 hrs, then the solid was recovered and washed with deionized water. This exchange and wash procedure was repeated one additional time. Elemental analysis of the product gave the following composition as weight % of the oxides: 3.76% $K_2O$, 10.02% $Na_2O$, 24.40% $Al_2O_3$ and 62.00% $SiO_2$. The Na and K contents of the sample comprised approximately 80% and 20%, respectively, of the ion exchange capacity.

EXAMPLE 9

Preparation of a 99% Sodium Exchanged Synthetic Chabazite

A sample of sodium exchanged chabazite was prepared by ion exchange of a portion of the K-chabazite sample prepared above in Example 7. 50 gms of the dried K-chabazite was humidified, added to 1665 ml of 1M $NaNO_3$ solution at 95°–100° C. for 2 hrs, then the solid was recovered and washed with deionized water. This exchange and wash procedure was repeated five additional times. Elemental analysis of the product gave the following composition as weight percent of the oxides: 0.23% $K_2O$, 12.37% $Na_2O$, 24.50% $Al_2O_3$ and 62.80% $SiO_2$. The Na and K contents of the sample comprised approximately 99% and 1%, respectively, of the ion exchange capacity.

EXAMPLE 10

Calcination of an Ammonium Exchanged Synthetic Chabazite

A sample of the ammonium exchanged chabazite prepared in Example 2 was calcined in air at 350° C. The dried product from Example 2 was placed in a muffle furnace at 110° C., then raised at about 5° C./min to 350° C. and held there for 2 hrs. Elemental analysis of the calcined product gave the following composition as weight percent of the oxides: 2.46% $K_2O$, 0.02% $Na_2O$, 29.20% $Al_2O_3$ and 68.30% $SiO_2$.

EXAMPLES 11–15

Calcination of Cation Exchanged Synthetic Chabazites

Samples of the cation exchanged chabazites prepared in Examples 4,5,6, 8 and 9 were individually calcined at 450° C. using the general procedure given in Example 10. The treatment process is shown in Table 1.

TABLE 1

| EXAMPLES | STARTING MATERIAL | PRECURSOR | CALCINATION ATMOSPHERE |
|---|---|---|---|
| EXAMPLE 11 | Example 4 | LZY62 | AIR |
| EXAMPLE 12 | Example 5 | LZY62 | AIR |
| EXAMPLE 13 | Example 6 | LZY64 | AIR |
| EXAMPLE 14 | Example 8 | LZY64 | AIR |
| EXAMPLE 15 | Example 9 | LZY64 | 100% Steam |

EXAMPLES 16–21

Geometric Selectivity and Shape Selectivity Indexes

Several catalysts were measured with respect to GSI and SSI in accordance with the sorption procedures described. More specifically, the GSI was determined by measuring the sorption of methanol and 1-PrOH on the catalyst system when exposed to sorbate vapors at 20° C. for a period of 20–24 hours. In determining the geometric selectivity index (GSI) the general procedure of U.S. Pat. No. 4,737,592 was followed. In determining the Shape Selectivity Index (SSI) Each catalyst sample was outgassed, in situ, at a rate of 1° C. per minute to a temperature of 400° C. and held under vacuum of 0.1 millitorr for 10–12 hours. Each catalyst sample was then cooled to 20° C. and exposed to the respective vapor for about 24 hours at a relative pressure ($p/p_o$) of 0.5. The temperature for sorption of methanol, 1-PrOH and 2-PrOH was 20° C. The order of sorption for each of the catalyst systems was 2-PrOH, 1-PrOH and methanol. After exposure to each of the sorbate vapors, the test catalysts were degassed overnight at 400° C. under vacuum and the catalyst sample weighed to determine whether all of the sorbate vapor had been removed. If some sorbate vapor remained, and the original dry weight of the catalyst system was not reached, the test catalyst was again outgassed. The corresponding indexes were calculated.

Table 2 below sets forth the synthetic and natural catalyst systems and their corresponding GSI and SSI values. The natural chabazites are used for illustrative purposes only. By their very nature minerals differ not only between natural deposits, but within a deposit.

TABLE 2

| EXAMPLES | CATALYST | MEOH (mmol/g) | N-PROH (mmol/g) | I-PROH (mmol/g) | GSI | SSI |
|---|---|---|---|---|---|---|
| EX 1 | 100% KChab | 5.19 | 2.29 | 0.10 | 1.21 | 22.90 |
| EX 3 | 95% KChab | 5.10 | 1.53 | 0.10 | 1.78 | 15.30 |
| EX 4 | 58% NaChab | 5.03 | 2.33 | 0.33 | 1.15 | 7.06 |
| EX 5 | 99% NaChab | 6.24 | 3.03 | 0.14 | 1.10 | 21.64 |
| EX 10 | 11% KChab | 4.49 | 1.48 | 0.16 | 1.62 | 9.25 |
| EX 11 | 58% NaChab | 5.05 | 2.33 | 0.25 | 1.16 | 9.32 |
| EX 12 | 99% NaChab | 5.21 | 1.81 | 0.12 | 1.53 | 15.08 |
| EX 13 | 66% NaChab | 6.15 | 2.95 | 0.42 | 1.11 | 7.02 |
| EX 15 | 99% NaChab | 1.66 | 0.15 | 0.10 | 5.90 | 1.50 |
| EX 16 | DURKEE* | 5.94 | 0.94 | 0.23 | 3.37 | 4.09 |
| EX 17 | NOVA SCOTIA* | 7.14 | 1.20 | 0.05 | 3.19 | 23.90 |
| EX 18 | CHRISTMAS* | 5.06 | 2.39 | 0.51 | 1.13 | 4.69 |
| EX 19 | BOWIE* | 6.36 | 2.97 | 0.76 | 1.14 | 3.91 |
| EX 20 | BUCKHORN* | 4.61 | 1.36 | 0.17 | 1.81 | 8.00 |
| EX 21 | LZY62 | 5.90 | 3.11 | 2.87 | 1.01 | 1.08 |

*These are naturally occurring zeolites.

EXAMPLE 22

Methanol Amination: Chabazite Catalysts

Several methanol aminations were carried out by reacting methanol with ammonia utilizing various catalyst systems. Table 3 sets forth the catalyst description, its origin and the reaction conditions, and Table 4 sets forth the results of each reaction.

TABLE 3

| | | Catalysts & Reaction Conditions | | | | |
|---|---|---|---|---|---|---|
| RUN | CATALYST EXAMPLES | TYPE CATALYSTS | Mole Ratio N/R | GHSV (1/hr) | Temp (°C.) | Pressure (PSIG) |
| 1 | EX 1 | 100% KChab uncalcined | 3.5 | 1000 | 350 | 250 |
| | | | | | 375 | 250 |
| 2 | EX 3 | 95% KChab uncalcined | 3.5 | 1000 | 350 | 250 |
| | | | 3.5 | 500 | 350 | 250 |
| | | | 2.3 | 1000 | 350 | 250 |
| | | | 2.3 | 500 | 350 | 250 |
| 3 | EX 4 | 58% NaChab uncalcined | 3.5 | 1000 | 350 | 250 |
| | | | 3.5 | 500 | 350 | 250 |
| 4 | EX 5 | 99% NaChab uncalcined | 3.5 | 1000 | 350 | 250 |
| | | | 3.5 | 500 | 350 | 250 |
| 5 | EX 11 | 58% NaChab calcined | 3.5 | 1000 | 350 | 250 |
| 6 | EX 12 | 99% NaChab calcined | 3.5 | 1000 | 350 | 250 |
| 7 | EX 13 | 66% NaChab calcined | 3.5 | 1000 | 350 | 250 |
| 8 | EX 15 | 99% NaChab calcined | 3.5 | 1000 | 350 | 250 |

TABLE 4

| | | | Reaction Conditions and Results | | | | | |
|---|---|---|---|---|---|---|---|---|
| RUN | N/R | GHSV | (°C.) | (PSIG) | GSI | SSI | MeOH CONV % | % TMA SEL. |
| 1 | 3.5 | 1000 | 350 | 250 | 1.21 | 22.90 | 51 | 6 |
| | 3.5 | 1000 | 375 | 250 | | | 62 | 5 |
| 2 | 3.5 | 1000 | 350 | 250 | 1.78 | 15.30 | 65 | 7 |
| | 3.5 | 500 | 350 | 250 | | | 86 | 6 |
| | 2.3 | 1000 | 350 | 250 | | | 62 | 5 |
| | 2.3 | 500 | 350 | 250 | | | 81 | 6 |
| 3 | 3.5 | 1000 | 350 | 250 | 1.15 | 7.06 | 94 | 33 |
| | 3.5 | 500 | 350 | 250 | | | 96 | 20 |
| 4 | 3.5 | 1000 | 350 | 250 | 1.10 | 21.64 | 76 | 4 |
| | 3.5 | 500 | 350 | 250 | | | 90 | 4 |
| 5 | 3.5 | 1000 | 350 | 250 | 1.16 | 9.32 | 98 | 15 |
| 6 | 3.5 | 1000 | 350 | 250 | 1.53 | 15.08 | 73 | 4 |
| 7 | 3.5 | 1000 | 350 | 250 | 1.11 | 7.02 | 99 | 13 |
| 8 | 3.5 | 1000 | 350 | 250 | 5.90 | 1.50 | 34 | 1 |

Figure 3:
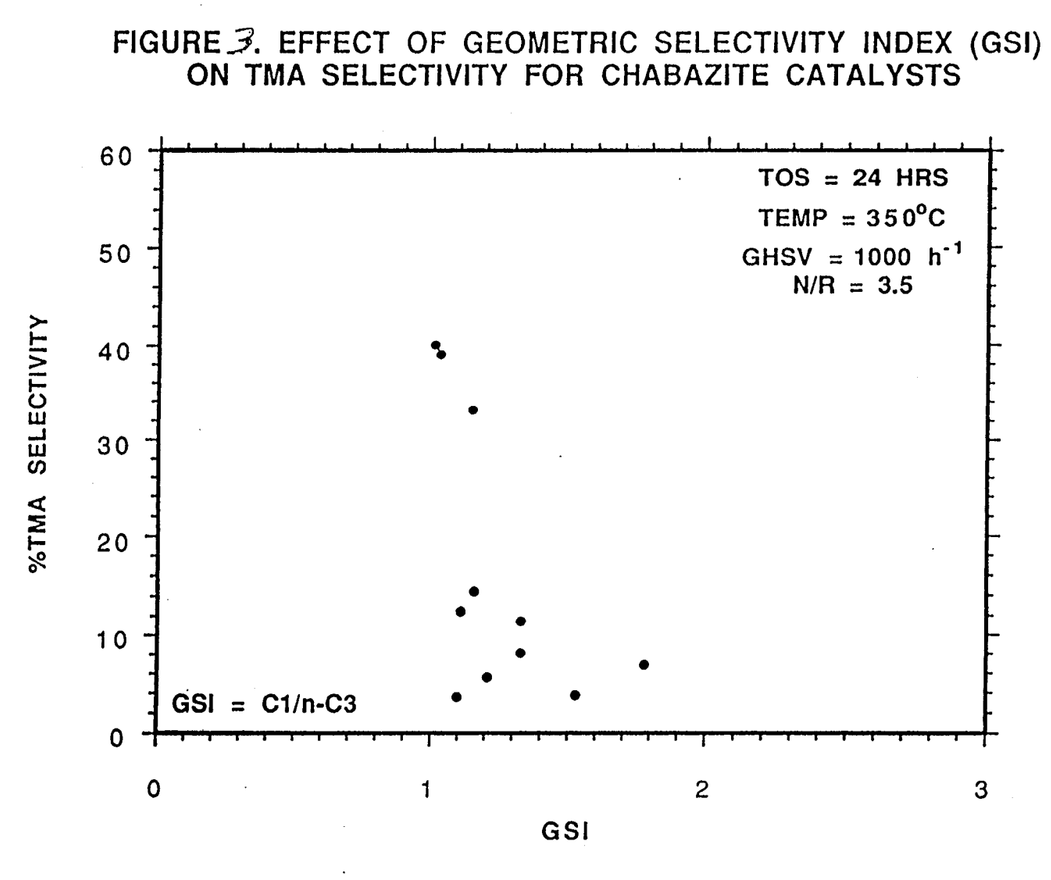
FIG. 3 is a plot of geometric selectivity index (GSI) vis-a-vis the TMA selectivity for synthetic chabazite catalysts as compared to natural chabazite catalysts.

By contrast, FIG. 3 shows the geometric selectivity index (GSI) vis-a-vis TMA selectivity for synthetic chabazite catalysts. From the plot, it is shown that the excellent selectivity and activity regarding methylamine production can be achieved with a low GSI. Therefore, SSI is a more valuable parameter on which to base catalyst performance.

SUMMARY

Runs 1 and 4 show the effect of cation type in uncalcined catalysts on methanol conversion and TMA selectivity. Runs 4 and 6 at 99+% cation exchange levels show the Na cation form at high SSI values afford higher conversions than the K cation form (Run 2). The Na and K exchanged catalysts have SSI values of about 22 and 23, respectively, and afford TMA selectivities that are much less than equilibrium values of 35 wt %. The catalysts gave GSI values less than 3. With such similar SSI values, the difference in conversion reflects the cation type, not pore diffusion resistance.

Runs 1 and 2 show that the methanol conversion of the K cation form can be increased by partially exchanging $NH_4^+$ for $K^+$ even though the GSI is less than 3. By maintaining an SSI value greater than about 7 for these uncalcined catalysts. TMA selectivities are still very low. This effect is also seen for the Na cation form by comparing Runs 3 and 4 where conversion increases from 76% to 94% while TMA is still less than 35 wt %.

Runs 7 and 8 for the 99% Na chabazite show that SSI values of less than 3 are not desirable for methylamines synthesis. Run 8 utilized a catalyst with 1-PrOH sorption capacity of less than 0.5 mmol/g. In this case the low SSI value results from significant exclusion of both 1-PrOH and 2-PrOH, whereas its GSI of about 6 indicates that methanol is still highly accessible. According to the prior art this would be an acceptable catalyst since its TMA selectivity is only 1 wt % indicating that its activity is still dominated by the zeolite interior surface. However, its conversion (34%) is unacceptable, i.e., less than 50% at 350° C.

Runs 3 and 5, and 4 and 6 show the effect of calcination. For Runs 3 and 5 the GSI values for the 58% uncalcined and calcined Na chabazites remain less than 3 but the SSI increased from 7 to 9 with calcination resulting in a decrease of TMA selectivity from 33 wt % to 15 wt %. Meanwhile, the conversion increased from 94% to 98%. Run 3 shows uncalcined catalyst to be extremely active but relatively non-selective with respect to TMA as compared to the calcined form. At very high SSI values, e.g., >25, it is expected that pore diffusion resistance might limit both conversion and TMA selectivity catalysis would be limited to surface catalysis and the product slate would approach that of an equilibrium distribution. In Runs 4 and 6 where the catalyst has greater than about 99% of its ion exchangeable cation as Na and the SSI values are 22 and 15, respectively, calcination at 450° C. has little or no effect on conversion or TMA selectivity.

Runs 5, 6 and 7 show the effect of cation exchange in a series of calcined catalysts with GSI values less than 3 and SSI values which range from 7 to 15. Decreasing the Na cation exchange from 99% to 66% causes an increase in conversion from 73% to 99% and an increase in TMA selectivity from 4 wt % to 13 wt %. Further decreasing the Na exchange from 66% to 58% shows no conversion benefit under the stated process conditions and a small increase in TMA selectivity from 13 wt % to 15 wt %.

Figure 1:
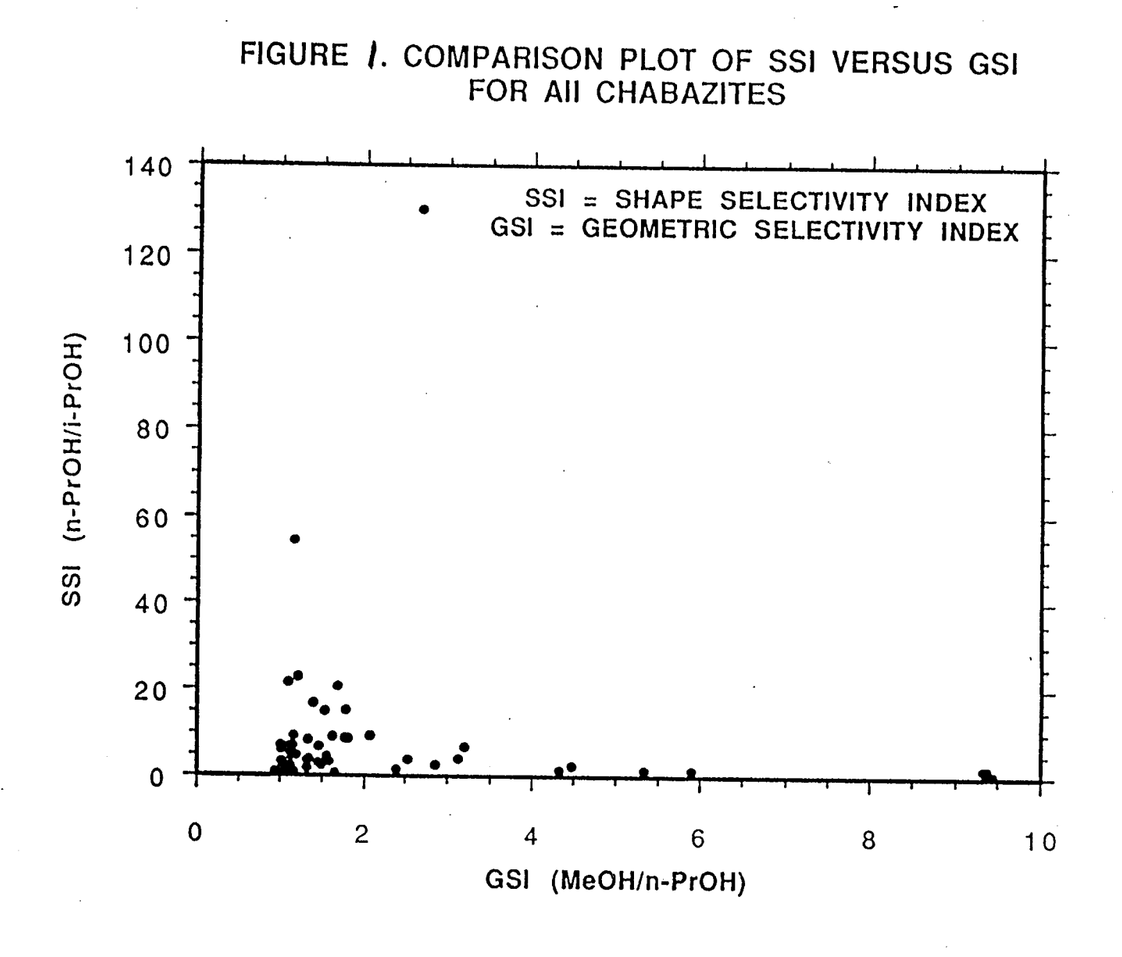
FIG. 1 is a plot showing the correlation between SSI and GSI for a large number of chabazite catalysts, including calcined and uncalcined catalysts.
Figure 2:
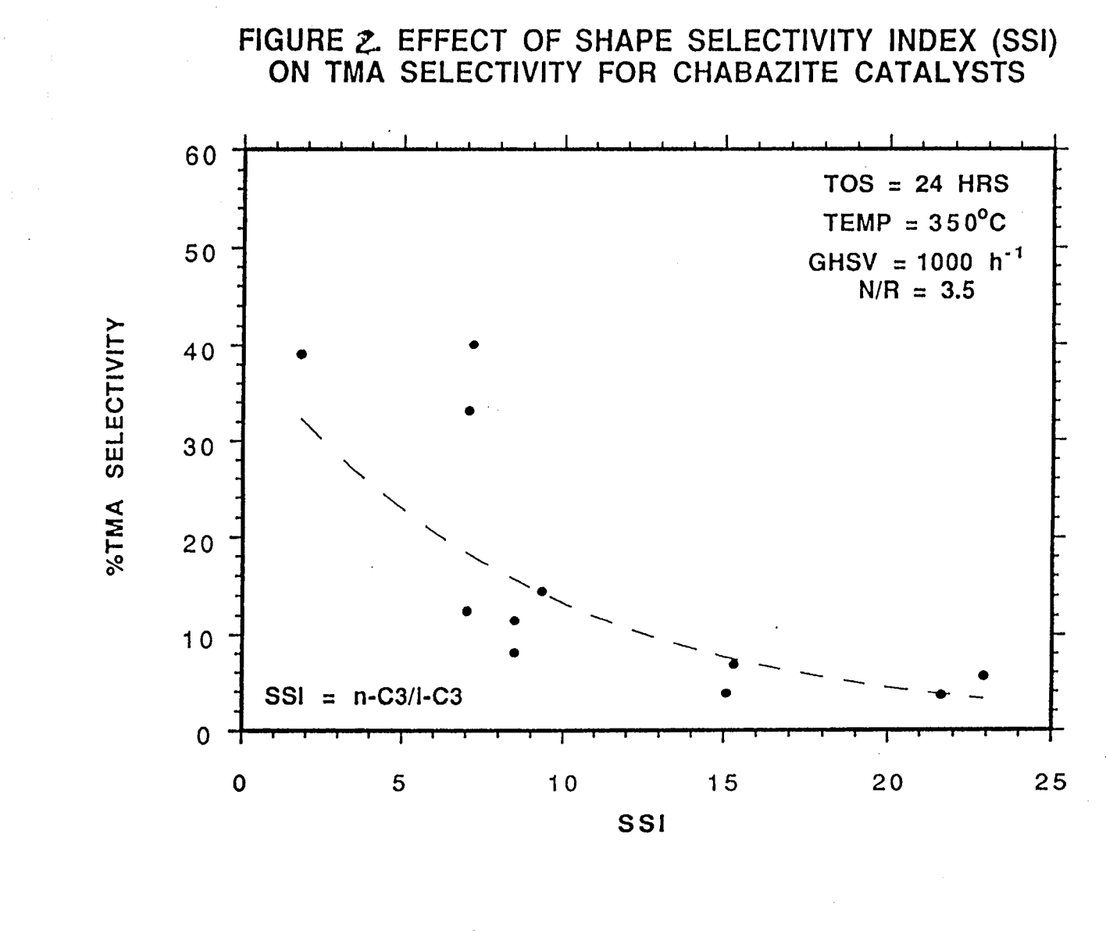
FIG. 2 is a plot showing the relationship of shape selectivity index (SSI) on the TMA selectivity for both calcined and uncalcined chabazite catalysts.

FIGS. 1–3 were generated from the data obtained from the above runs for the purpose of pictorially evaluating SSI as a tool for forecasting amination product slate. FIG. 1 is a drawing comprising a plot of the data from Tables 3 and 4. It shows an absence of correlation between SSI and GSI for a large number of chabazite catalysts. FIG. 2 is a plot of SSI and TMA selectivity and shows the inverse effect of SSI on the TMA selectivity for both calcined and uncalcined chabazite catalysts. From FIG. 2 as the SSI value increases, the size and/or shape of the microporous structure preferentially excludes 2-PrOH to a greater extent than 1-PrOH. Thus, an uncalcined catalyst with an SSI of about 7 or larger may afford TMA selectivities of 35 wt % or less. A calcined catalyst with SSI of about 3 or larger will afford similar results.

EXAMPLE 23

Methanol Amination: Comparative and Base Treatment Studies

A series of comparative methanol aminations were carried out by reacting methanol with ammonia utilizing various catalyst systems.

The base treated chabazite was prepared by placing a 20 g sample of K-Chabazite in 200 ml of a 0.5M KOH and heated to 100° C. without stirring for a period of 2 hours. The solution was drained from the solid washed with deionized water for about 5 minutes. The treatment was repeated except that the mixture was held at 100° C. for 16 hours. After washing with distilled water and drying, the sample was analyzed to contain 21.2% $Al_2O_3$, 57.7% $SiO_2$ and 17.37% $K_2O$.

The sample then was humidified by placing in a closed vessel with a petri dish filled with water for 16 hr. The sample was treated three times with 30% $NH_4Cl$ (10 ml/g) at 100° C. for 1 hour. After each treatment the sample was washed with $H_2O$ for 10 minutes. The exchanged sample was dried at 110° C. and calcined at 450° C. for 2 hours.

Table 5 sets forth the catalyst description, its origin and the results of each reaction. All runs were performed at 350° C., GHSV=1000 $hr^1$, N/R=3.5 and Pressure=250 psig., except where specified.

TABLE 5

| RUN | EXAMPLES | CATALYST | ORIGIN | GSI | SSI | % CONV | % MMA | % DMA | % TMA |
|---|---|---|---|---|---|---|---|---|---|
| 1 | AMORPHOUS | $Al_2O_3/SiO_2$ | AKZO | N/A | N/A | 77 | 39 | 23 | 38 |
| 2 | NATURAL CHABAZITE | HFORM | AW500 | 1.03 | 1.81 | 97 | 36 | 25 | 39 |
| 3 | SYNTHETIC CHABAZITE | HFORM | LZY64 | N/A | N/A | 98 | 37 | 26 | 37 |
| 4 | SYNTHETIC Treatment CHABAZITE | Base $H^+$ *300° C. | LZY64 | 2.21 | 12.5 | 96.7 | 44.1 | 48.7 | 7.2 |
| 5. | SYNTHETIC Treatment CHABAZITE | Base $H^+$ *350° C. | LZY62 | 2.21 | 12.5 | 94.2 | 23.1 | 51.5 | 25.4 |

Runs 1 and 2 of Table 5 show comparative data for an amorphous silica-alumina catalyst and an H Form of AW500 natural chabazite. The 1-PrOH sorption for the H Form of natural chabazite is high at 2.39 mmol/g. Thus, this data shows that while the H Form of natural chabazite can afford improved conversions over the amorphous catalyst (it is more active) or certain synthetic chabazites, with a GSI less than 3 and SSI less than 5 it gives a TMA selectivity which is similar to that of the amorphous catalyst of Run 1.

Runs 2 and 3 of Table 5 are comparative Examples that show similar, high conversions and nonselective methylamines distribution are obtained for the H-forms of both natural and synthetic chabazites. No shape selectivity is introduced. Runs 4 and 5 use the shape selective H form base treated catalyst. It has the H+ ion positioned within the framework for enhanced reaction and shape selectivity.

The calcined synthetic chabazites having an SSI of from 5 to 25 afforded the highest methanol conversions and essentially the lowest percent TMA selectivity. In contrast, the chabazites having a GSI greater than 3, although effective, were not as catalytically active.

The importance of the SSI value, particularly as the number exceeds about 5, demonstrates the importance of SSI in terms of methanol/dimethylether conversion rate and percent TMA selectivity. For example, for a synthetic chabazite having an SSI toward the lower end of the range, as for example the uncalcined synthetic chabazites, the percent TMA selectivity increases substantially, and the catalyst remains highly active.

EXAMPLE 24

Monomethylamine Feedstock Reforming

The procedure of Example 23 was repeated except that monomethylamine containing feedstocks were substituted for methanol as the feedstock. One feedstock contained about 30% monomethylamine in ammonia, another contained pure monomethylamine. The catalyst employed in the reaction was a hydrogen/potassium exchanged chabazite similar to base treated chabazite of Example 23. Table 6 sets forth the reaction conditions and results.

TABLE 6

MMA REFORMING OVER CHABAZITE CATALYSTS
Reaction Conditions and Results

|  | NH$_3$/MeOH | 30% MMA* | Pure MMA | Pure MMA |
|---|---|---|---|---|
| % Conv | 94.9 | 91.5 |  |  |
| MMA | 26.4 | 28.8 | 23.9 | 19.6 |
| DMA | 69 | 66.2 | 72.4 | 72 |
| TMA | 4.6 | 5 | 3.7 | 8.4 |
| Temp | 300 | 300 | 300 | 300 |
| N/R | 1 | 1 | 1 | 1 |
| GHSV | 1000 | 1000 | 1000 | 500 |

*Feedstock contained 30% MMA in NH$_3$

The above results show excellent conversion and excellent selectivity of monomethylamine to dimethylamine over the chabazite catalyst. Little TMA is produced. The results show the addition of ammonia to the monomethylamine feed did not inhibit conversion significantly.

What is claimed is:

1. In a process for the production of a non-equilibrium mixture of methylamines comprising monomethylamine, dimethylamine, and trimethylamine by the catalytic reaction of a feedstock consisting methanol and dimethylether with ammonia, in the presence of a microporous catalyst, the improvement for enhancing the methanol or dimethylether conversion and reducing the production of trimethylamine in the methylamine reaction product, which comprises utilizing a catalyst having a geometric selectivity index less than about 3, a shape selective index of at least about 5 and a 1-PrOH sorption of at least about 0.5 mmol/g.

2. The process of claim 1 wherein the said microporous catalyst consists essentially of a synthetic chabazite and methanol and ammonia are employed in said reaction.

3. The process of claim 2 wherein the said microporous catalyst consists essentially of a calcined, synthetic chabazite catalyst.

4. The process of claim 3 wherein the reaction is performed in the temperature range 250° to 375° C. and an N/R ratio of 0.2 to 10.

5. The process of claim 4 wherein the reaction is performed in the pressure range 50 to 1000 psig.

6. The process of claim 5 wherein the reaction is performed with a GHSV range of 200 to 8000 hr$^1$.

7. The process of claim 6 where n the reaction is performed with an N/R in the range 1 to 5.

8. The process of claim 7 wherein the cations in the synthetic chabazite are a mixture of cation selected from the group consisting of H, Li, Na, K, Rb, Cs, Mg, Ca, Ba, Al, Ga, Fe, Sr, La, Cu, Zn, Ni, B, Ce, Sn, and Ru.

9. The process of claim 3 comprising a calcined chabazite catalyst having an SSI in the range 7 to 25, and said process is performed at a temperature of 250-375° C., a pressure of 150 to 500 psig, N/R of 1 to 5 and a GHSV of 500 to 5000 hr$^1$.

10. The process of claim 9 wherein the cations in the synthetic chabazite are predominantly alkali metal ions selected from the group consisting of H, Li, Na, K, Rb and Cs.

11. The process of claim 9 wherein the cations in the synthetic chabazite are predominantly alkaline earth metal ions selected from the group consisting of Mg, Ca, Sr and Ba.

12. The process of claim 9 wherein the cations in the synthetic chabazite are predominantly metal ions selected from the group consisting of Al, Ga, B and Fe.

13. In a process for the production of a mixture of methylamines comprising monomethylamine, dimethylamine, and trimethylamine by the catalytic reforming of a feedstock containing monomethylamine in the presence of a catalyst, the improvement for reducing the production of trimethylamine in the reaction product, which comprises effecting reforming in the presence of a microporous catalyst having a geometric selectivity index less than about 3, a shape selective index of at least about 5 and a 1-PrOH sorption of at least about 0.5 mmol/g.

14. The process of claim 13 wherein the microporous catalyst consists essentially of a synthetic chabazite.

15. The process of claim 13 wherein the said microporous catalyst consists essentially of a calcined, synthetic chabazite catalyst.

16. The process of claim 15 wherein the reaction is performed in the temperature range 250° to 375° C. and an N/R ratio of 0.2 to 10.

17. The process of claim 16 wherein the reaction is performed in the pressure range 50 to 1000 psig.

18. The process of claim 17 wherein the reaction is performed with a GHSV range of 200 to 8000 hr$^1$.

19. The process of claim 18 wherein the reaction is performed with an N/R in the range 1 to 5.

20. The process of claim 19 wherein the cations in the synthetic chabazite are predominantly alkali metal ions selected from the group consisting of H, Li, Na, K, Rb and Cs.

21. The process of claim 20 wherein the cations in the synthetic chabazite are predominantly alkaline earth metal ions selected from the group consisting of Mg, Ca, Sr and Ba.

* * * * *